United States Patent [19]
Miziorko

[11] Patent Number: 5,668,001
[45] Date of Patent: Sep. 16, 1997

[54] 3-HYDROXY-3-METHYL-GLUTARYL-COA SYNTHASE PREPARATION WITH IMPROVED STABILITY

[75] Inventor: Henry M. Miziorko, Elm Grove, Wis.

[73] Assignee: MCW Research Foundation, Inc., Milwaukee, Wis.

[21] Appl. No.: 305,505

[22] Filed: Sep. 13, 1994

Related U.S. Application Data

[63] Continuation of Ser. No. 72,040, Jun. 2, 1993, abandoned.

[51] Int. Cl.$^6$ .............. C12N 9/88; C12N 15/60; C12N 15/70; C12Q 1/527
[52] U.S. Cl. .............. 435/232; 435/4; 435/69.1; 435/252.33; 435/320.1; 435/14; 435/29; 435/73
[58] Field of Search .............. 435/69.1, 232, 435/252.33, 320.1, 252.3, 4; 536/23.2

[56] References Cited

PUBLICATIONS

Greenspan, et al., "Inhibition of 3 hydroxy–3–methylglutaryl–CoA synthase and cholesterol biosynthesis by β–lactone inhibitors and binding of these inhibitors to the enzyme", *Biochem. J.*, 289:889–895, 1993.
Ayté, et al., "Rat mitochondrial and cytosolic 3–hydroxy–3–methylglutaryl–CoA synthases are encoded by two different genes", *Proc. Nat'l. Acad. Sci. USA*, 87:3874–3878, 1990.
Kattar–Cooley, et al., "Avian Liver 3–Hydroxy–3–methylglutaryl–CoA Synthase: Distinct Genes Encode the Cholesterogenic and Ketogenic Isozymes", *Arch. Biochem. Biophys.*, 283:523–529, 1990.
Misra, et al., "Avian 3–Hydroxy–3–methylglutaryl–CoA Synthase", *Journ. Biol. Chem.*, 268:12129–12135, 1993.
Russ, et al., "Amplification and direct sequencing of a cDNA encoding human cytosolic 3–hydroxy–3–methylglutaryl–coenzyme A synthase", *Biochmica et Biophysica Acta*, 1132:329–331, 1992.
Abstract for ASBMB/DBC–ACS meeting, published in *FASEB J.* 7[7]:A1176, Apr., 1993.
Roberts, J.R., et al., *Journal of Biological Chemistry*, 269(27):17841–17846, 1994.
Zhang, Z., et al., *Journal of Biological Chemistry*, 267(3):1484–1490, 1992.
1993 Novagen, Inc., Products Catalogue, pp. 1, 36–47.
Studier, W, et al., 1990, Methods in Enzymology, 185:60–89.
Ayte et al (1990) Proc. Natl. Acad. Sci. 87, 3874–3878.
Greenspan et al (1993) Biochem J. 289, 889–895.
Kattar–Cooley et al (1990) Arch. Biochem. Biophys. 283, 523–529.
Oimura et al (1987) J. Antibiotics, vol. XL pp. 1356–1357.
Clickenbeard et al (1975) J. Biol. Chem. 250, 3124–3135.
Wang et al (1988) J. Parenteral. Sci & Technol. 42(25), 54–526.
Sambrook et al in "Molecular Cloning: A Laboratory Manual" Cold Spring Harbor Lab. Press, (1989) pp. 17.1–17.44.

*Primary Examiner*—Robert A. Wax
*Assistant Examiner*—William W. Moore
*Attorney, Agent, or Firm*—Quarles & Brady

[57] ABSTRACT

A preparation of recombinant 3-hydroxy-3-methylglutaryl-CoA synthase is disclosed, wherein the preparation has at least 0.024 units/mg specific activity. Preferably, the preparation has at least 0.24 units/mg specific activity and is a crude cell extract. Preferably, at least 90% of the synthase molecules have not been substantially proteolytically cleaved. A preparation of recombinant HMG-CoA synthase wherein the preparation retains 50% activity after storage at 4° C. for six months is also disclosed. A method of evaluating the efficacy of candidate anti-isoprene and anti-cholesterol drugs is also disclosed which comprises exposing the candidate drug to a recombinant 3-hydroxy-3-methylglutaryl CoA synthase preparation.

5 Claims, 6 Drawing Sheets

FIG. 1A

|  | 1 |  |  |  | 50 |
|---|---|---|---|---|---|
| Hmcs$Crigr | .......... | .......... | .......... | ......MPG | SLPLNAEACW |
| Hmcs$Rat | .......... | .......... | .......... | ......MPG | SLPLNAEACW |
| Synthase | .......... | .......... | .......... | ......MPG | SLPLNAEACW |
| Avcytsyn | .......... | .......... | .......... | ......MPG | SLPVNTESCW |
| Hmcm$Rat | MQRLLAPARR | VLQVKRVMQE | SSLSPAHLLP | AAQQRFSTIP | PAPLAKTDTW |

|  | 51 |  |  |  | 100 |
|---|---|---|---|---|---|
| Hmcs$Crigr | PKDVGIVALE | IYFPSQYVDQ | AELEKYDGVD | AGKYTIGLGQ | ARMGFCTDRE |
| Hmcs$Rat | PKDVGIVALE | IYFPSQYVDQ | AELEKYDGVD | AGKYTIGLGQ | ARMGFCTDRE |
| Synthase | PKDVGIVALE | IYFPSQYVDQ | AELEKYDGVD | AGKYTIGLGQ | AKMGFCTDRE |
| Avcytsyn | PKDVGIVALE | IYFPSQYVDQ | TELEKYDGVD | AGKYTIGLGQ | SKMGFCSDRE |
| Hmcm$Rat | PKDVGILALE | VYFPAQYVDQ | TDLEKFNNVE | AGKYTVGLGQ | TRMGFCSVQE |

|  | 101 |  |  |  | 150 |
|---|---|---|---|---|---|
| Hmcs$Crigr | DINSLCLTVV | QNLMERNSLS | YDCIGRLEVG | TETIIDKSKS | VKSNLMQLFE |
| Hmcs$Rat | DINSLCLTVV | QKLMERNSLS | YDCIGRLEVG | TETIIDKSKS | VKSNLMQLFE |
| Synthase | DINSLCMTVV | QNLMERNNLS | YDCIGRLEVG | TETIIDKSKS | VKTNLMQLFE |
| Avcytsyn | DINSLCLTVV | QKLMERNSLS | YDCIGRLEVG | TETIIDKSKS | VKTVLMQLFE |
| Hmcm$Rat | DINSLCLTVV | QRLMERTKLP | WDAVGRLEVG | TETIIDKSKA | VKTVLMELFQ |

|  | 151 |  |  |  | 200 |
|---|---|---|---|---|---|
| Hmcs$Crigr | ESGNTDIEGI | DTTNACYGGT | AAVFNAVNWI | ESSSWDGRYA | LVVAGDIAIY |
| Hmcs$Rat | ESGNTDIEGI | DTTNACYGGT | AAVFNAVNWI | ESSSWDGRYA | LVVAGDIAIY |
| Synthase | ESGNTDIEGI | DTTNACYGGT | AAVFNAVNWI | ESSSWDGRYA | LVVAGDIAVY |
| Avcytsyn | ESGNTDVEGI | DTTNACYGGT | AALFNAINWI | ESSSWDGRYA | LVVAGDIAVY |
| Hmcm$Rat | DSGNTDIEGI | DTTNACYGGT | ASLFNAANWM | ESSYWDGRYA | LVVCGDIAVY |

|  | 201 |  |  |  | 250 |
|---|---|---|---|---|---|
| Hmcs$Crigr | ATGNARPTGG | VGAVALLIGP | NAPLIFDRGL | RGTHMQHAYD | FYKPDMLSEY |
| Hmcs$Rat | ASGNARPTGG | VGAVALLIGP | NAPVIFDRGL | RGTHMQHAYD | FYKPDMLSEY |
| Synthase | ATGNARPTGG | VGAVALLIGP | NAPLIFERGL | RGTHMQHAYD | FYKPDMLSEY |
| Avcytsyn | ATGNARPTGG | AGAVAMLVGS | NAPLIFERGL | RGTHMQHAYD | FYKPDMVSEY |
| Hmcm$Rat | PSGNPRPTGG | AGAVAMLIGP | KAPLVLEQGL | RGTHMENAYD | FYKPNLASEY |

|  | 251 |  |  |  | 300 |
|---|---|---|---|---|---|
| Hmcs$Crigr | PIVDGKLSIQ | CYLSALDRCY | SVYRKKIRAQ | WQKEGNDNDF | TLNDFGFMIS |
| Hmcs$Rat | PVVDGKLSIQ | CYLSALDRCY | SVYRKKIRAQ | WQKEGKDKDF | TLNDFGFMIF |
| Synthase | PIVDGKLSIQ | CYLSALDRCY | SVYCKKIHAQ | WQKEGNDKDF | TLNDFGFMIF |
| Avcytsyn | PVVDGKLSIQ | CYLSALDRCY | SVYRNKIHAQ | WQKEGTDRGF | TLNDFGFMIF |
| Hmcm$Rat | PLVDGKLSIQ | CYLRALDRCY | AAYRRKIQNQ | WKQAGNNQPF | TLDDVQYMIF |

FIG. 1B

```
               301                                                              350
Hmcs$Crigr   HSPYCKLVQK  SLARMFLNDF  LNDQNRDK.N  SIYSGLEAFG  DVKLEDTYFD
Hmcs$Rat     HSPYCKLVQK  SLARMFLNDF  LNDQNRDK.N  SIYSGLEAFG  DVKLEDTYFD
Synthase     HSPYCKLVQK  SLARMLLNDF  LNDQNRDK.N  SIYSGLEAFG  DVKLEDTYFD
Avcytsyn     HSPYCKLVQK  SVARLLLNDF  LSDQNAETAN  GVFSGLEAFR  DVKLEDTYFD
Hmcm$Rat     HTPFCKMVQK  SLARLMFNDF  LSS.SSDKQN  NLYKGLEAFK  GLKLEETYTN 351                                                              400
Hmcs$Crigr   RDVEKAFMKA  SSELFNQKTK  ASLLVSNQNG  NMYTSSVYGS  LASVLAQYSP
Hmcs$Rat     RDVEKAFMKA  SAELFNQKTK  ASLLVSNQNG  NMYTSSVYGS  LASVLAQYSP
Synthase     RDVEKAFMKA  SSELFSQKTK  ASLLVSNQNG  NMYTSSVYGS  LASVLAQYSP
Avcytsyn     RDVEKAFMKA  SAELFNQKTK  ASLLVSNQNG  NMYTPSVYGC  LASLLAQYSP
Hmcm$Rat     KDVDKALLKA  SLDMFNKKTK  ASLYLSTNNG  NMYTSSLYGC  LASLLSHHSA 401                                                              450
Hmcs$Crigr   QQLAGKRIGV  FSYGSGLAAT  LYSLKVTQDA  TPGSALDKVT  ASLCDLKSRL
Hmcs$Rat     QQLAGKRIGV  FSYGSGLAAT  LYSLKVTQDA  TPGSALDKIT  ASLCDLKSRL
Synthase     QQLAGKRIGV  FSYGSGLAAT  LYSLKVTQDA  TPGSALDKIT  ASLCDLKSRL
Avcytsyn     EHLAGQRISE  FSYGSGFAAT  LYSIRVTQDA  TPGSALDKIT  ASLSDLKARL
Hmcm$Rat     QELAGSRIGA  FSYGSGLAAS  FFSFRVSKDA  SPGSPLEKLV  SSVSDLPKRL 451                                                              500
Hmcs$Crigr   DSRTCVAPDV  FAENMKLRED  THHLANYIPQ  CSIDSLFEGT  WYLVRVDEKH
Hmcs$Rat     DSRTCVAPDV  FAENMKLRED  THHLANYIPQ  CSIDSLFEGT  WYLVRVDEKH
Synthase     DSRTGVAPDV  FAENMKLRED  THHLVNYIPQ  GSIDSLFEGT  WYLVRVDEKH
Avcytsyn     DSRKCIAPDV  FAENMKIRQE  THHLANYIPQ  CSVEDLFEGT  WYLVRVDEKH
Hmcm$Rat     DSRRRMSPEE  FTEIMNQREQ  FYHKVNFSPP  GDTSNLFPGT  WYLERVDEMH 501                                                              550
Hmcs$Crigr   RRTYARRPST  NDHNLGDGVG  LVHSNTATEH  IPSPAKKVPR  LPATAAESES
Hmcs$Rat     RRTYARRPST  NDHSLDEGVG  LVHSNTATEH  IPSPAKKVPR  LPATSGEPES
Synthase     RRTYARRPTP  NDDTLDEGVG  LVHSNIATEH  IPSPAKKVPR  LPATAAEPEA
Avcytsyn     RRTYARRPVM  GDGPLEAGVE  VVHPGIVHEH  IPSPAKKVPR  IPATTESEGV
Hmcm$Rat     RRKYARRPV.  ..........  ..........  ..........  ..........

551
Hmcs$Crigr   AV.ISNGEH
Hmcs$Rat     AV.ISNGEH
Synthase     AV.ISNGEH
Avcytsyn     TVAISNGVH
Hmcm$Rat     ..........
```

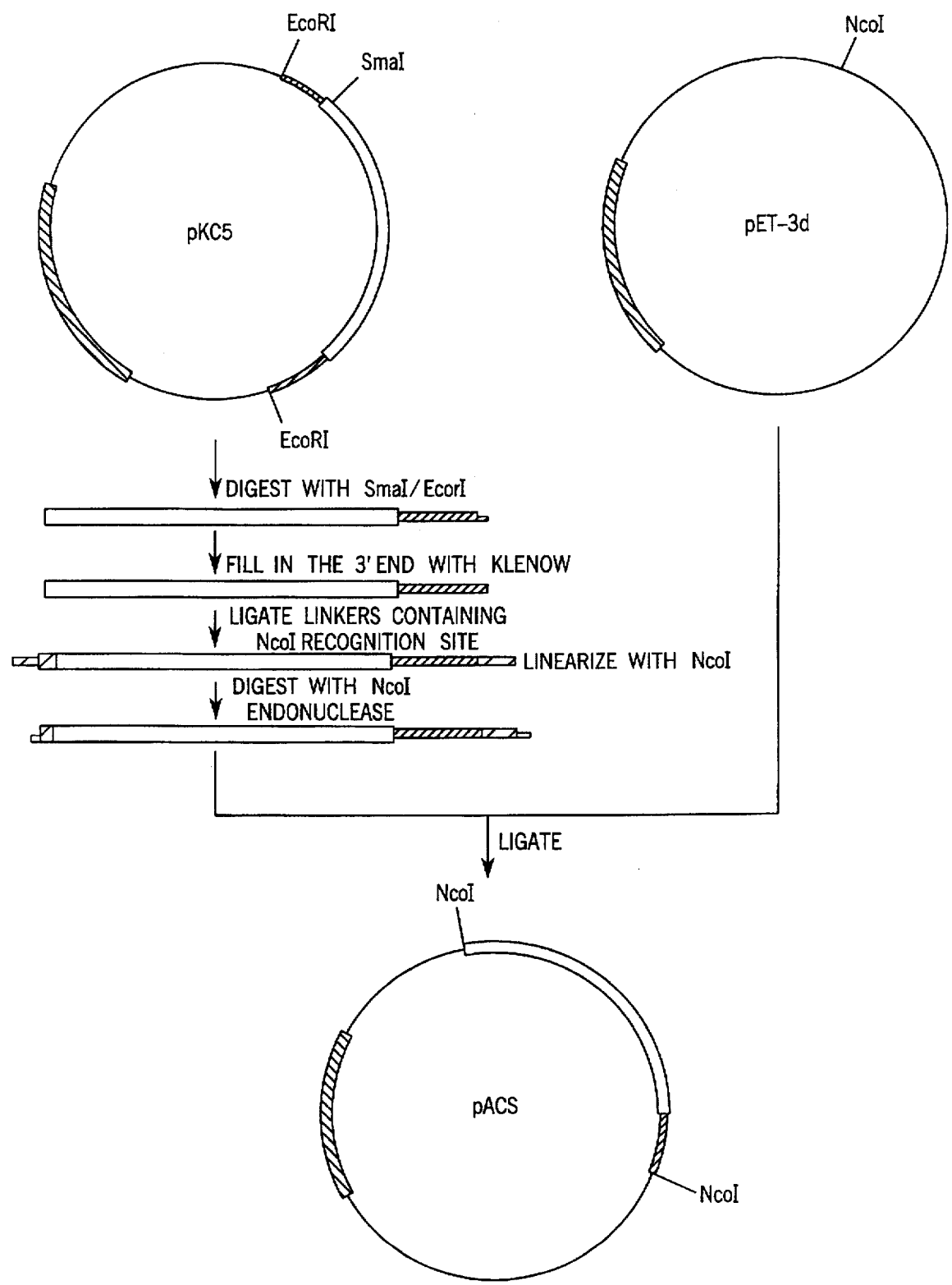

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1824 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CATGGCTGGG  TCTCTTCCAG  TGAACACTGA  ATCCTGCTGG  CCCAAAGATG  TGGGTATTGT      60

TGCACTGGAA  ATCTATTTTC  CCTCTCAGTA  TGTCGACCAG  ACTGAGCTGG  AGAAGTATGA     120

CGGTGTGGAT  GCAGGCAAAT  ACACCATTGG  GTTAGGCCAG  TCAAAGATGG  GCTTCTGCTC     180
```

| | | | | | |
|---|---|---|---|---|---|
| TGACCGAGAG | GATATCAATT | CCCTCTGTTT | GACTGTCGTT | CAGAAGCTTA | TGGAGAGGAA | 240 |
| CAGCCTTTCC | TATGACTGCA | TTGGGAGACT | GGAAGTTGGA | ACGGAGACAA | TAATTGATAA | 300 |
| ATCAAAATCG | GTGAAGACTG | TCCTGATGCA | GCTATTTGAA | GAATCTGGTA | ATACAGATGT | 360 |
| AGAAGGAATT | GACACAACCA | ATGCGTGCTA | TGGAGGCACT | GCTGCTCTTT | TTAATGCTAT | 420 |
| TAACTGGATT | GAGTCCAGTT | CTTGGGATGG | ACGCTATGCA | CTTGTTGTTG | CTGGAGACAT | 480 |
| TGCTGTGTAT | GCCACTGGAA | ATGCCAGGCC | AACAGGTGGA | GCTGGTGCTG | TTGCTATGCT | 540 |
| AGTTGGGTCA | AATGCTCCTT | TAATTTTTGA | GAGAGGATTG | CGTGGAACCC | ACATGCAGCA | 600 |
| TGCTTATGAC | TTCTATAAAC | CAGATATGGT | TTCTGAATAT | CCTGTAGTTG | ATGGCAAACT | 660 |
| ATCTATACAG | TGCTACCTCA | GTGCATTAGA | CCGCTGCTAT | AGTGTTATC | GCAATAAAAT | 720 |
| CCATGCCCAG | TGGCAAAAAG | AGGGGACAGA | CAGAGGTTTC | ACCTTGAATG | ATTTTGGATT | 780 |
| CATGATCTTT | CATTCTCCCT | ACTGTAAACT | GGTACAGAAG | TCGGTGGCAA | GACTGTTGCT | 840 |
| GAATGACTTT | CTCAGTGACC | AGAATGCAGA | AACAGCAAAT | GGTGTTTTCA | GTGGTCTGGA | 900 |
| AGCTTTCAGG | GATGTAAAGC | TTGAAGATAC | ATATTTTGAT | AGGGATGTGG | AAAAAGCTTT | 960 |
| TATGAAAGCT | AGTGCAGAGC | TCTTCAATCA | GAAAACCAAA | GCTTCCTTAC | TTGTGTCCAA | 1020 |
| TCAGAATGGA | AACATGTACA | CGCCTTCAGT | CTACGGTTGC | CTTGCTTCTC | TTCTAGCCCA | 1080 |
| GTACTCTCCA | GAGCACCTTG | CAGGACAAAG | AATCAGTGAG | TTCTCATATG | GCTCTGGTTT | 1140 |
| TGCTGCTACG | CTGTATTCCA | TCAGAGTTAC | ACAGGATGCC | ACTCCTGGTT | CTGCGCTTGA | 1200 |
| CAAAATAACT | GCTAGCCTTT | CTGATCTTAA | AGCAAGACTT | GACTCACGAA | ATGCATTGC | 1260 |
| ACCTGATGTC | TTTGCTGAAA | ACATGAAGAT | TAGACAGGAG | ACACATCACT | TGGCCAACTA | 1320 |
| TATTCCACAG | TGTTCAGTAG | AAGATCTCTT | TGAGGGAACA | TGGTATCTTG | TGCGTGTGGA | 1380 |
| TGAAAAACAC | AGGAGAACAT | ATGCACGACG | CCCAGTTATG | GGTGATGGAC | CCCTGGAGGC | 1440 |
| AGGAGTTGAA | GTTGTCCACC | CAGGCATTGT | TCATGAGCAC | ATCCCAAGCC | CTGCTAAGAA | 1500 |
| AGTGCCAAGA | ATCCCTGCAA | CAACAGAATC | TGAAGGCGTT | ACTGTTGCCA | TTTCCAATGG | 1560 |
| GGTGCATTAA | GATACCTCTG | TGAGGCAAGA | AAGAAGAAAC | TGGCCTTATG | AAAACTTGAA | 1620 |
| GTTCTGGGGT | CACAGTCTTT | GTGGACCTCC | CGGATCGTTC | TCTTTAATAT | TTCATTACAA | 1680 |
| AAAAATGGAA | AGAAAGACTT | GCTGGGGCTT | GTGGAAAATC | ATTATTTCAA | GGCTTTGTTT | 1740 |
| CAAGATAACT | TAAATGTTTT | CAGGTGGCAT | CTGTTCATAG | TGGAGAAATT | CATTCACAGC | 1800 |
| CTGTCTCAAA | TTAACTGAAT | TAGC | | | | 1824 |

(2) INFORMATION FOR SEQ ID NO:2:

( i ) SEQUENCE CHARACTERISTICS:
        ( A ) LENGTH: 522 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Pro Gly Ser Leu Pro Val Asn Thr Glu Ser Cys Trp Pro Lys Asp
 1               5                  10                  15

Val Gly Ile Val Ala Leu Glu Ile Tyr Phe Pro Ser Gln Tyr Val Asp
                20                  25                  30

Gln Thr Glu Leu Glu Lys Tyr Asp Gly Val Asp Ala Gly Lys Tyr Thr
            35                  40                  45

Ile Gly Leu Gly Gln Ser Lys Met Gly Phe Cys Ser Asp Arg Glu Asp
```

-continued

```
             50                          55                          60
Ile Asn Ser Leu Cys Leu Thr Val Val Gln Lys Leu Met Glu Arg Asn
 65                  70                  75                       80

Ser Leu Ser Tyr Asp Cys Ile Gly Arg Leu Glu Val Gly Thr Glu Thr
                 85                  90                  95

Ile Ile Asp Lys Ser Lys Ser Val Lys Thr Val Leu Met Gln Leu Phe
            100                 105                 110

Glu Glu Ser Gly Asn Thr Asp Val Glu Gly Ile Asp Thr Thr Asn Ala
            115                 120                 125

Cys Tyr Gly Gly Thr Ala Ala Leu Phe Asn Ala Ile Asn Trp Ile Glu
        130                 135                 140

Ser Ser Ser Trp Asp Gly Arg Tyr Ala Leu Val Ala Gly Asp Ile
145                 150                 155                 160

Ala Val Tyr Ala Thr Gly Asn Ala Arg Pro Thr Gly Gly Ala Gly Ala
                165                 170                 175

Val Ala Met Leu Val Gly Ser Asn Ala Pro Leu Ile Phe Glu Arg Gly
            180                 185                 190

Leu Arg Gly Thr His Met Gln His Ala Tyr Asp Phe Tyr Lys Pro Asp
        195                 200                 205

Met Val Ser Glu Tyr Pro Val Val Asp Gly Lys Leu Ser Ile Gln Cys
210                 215                 220

Tyr Leu Ser Ala Leu Asp Arg Cys Tyr Ser Val Tyr Arg Asn Lys Ile
225                 230                 235                 240

His Ala Gln Trp Gln Lys Glu Gly Thr Asp Arg Gly Phe Thr Leu Asn
            245                 250                 255

Asp Phe Gly Phe Met Ile Phe His Ser Pro Tyr Cys Lys Leu Val Gln
            260                 265                 270

Lys Ser Val Ala Arg Leu Leu Leu Asn Asp Phe Leu Ser Asp Gln Asn
            275                 280                 285

Ala Glu Thr Ala Asn Gly Val Phe Ser Gly Leu Glu Ala Phe Arg Asp
        290                 295                 300

Val Lys Leu Glu Asp Thr Tyr Phe Asp Arg Asp Val Glu Lys Ala Phe
305                 310                 315                 320

Met Lys Ala Ser Ala Glu Leu Phe Asn Gln Lys Thr Lys Ala Ser Leu
                325                 330                 335

Leu Val Ser Asn Gln Asn Gly Asn Met Tyr Thr Pro Ser Val Tyr Gly
            340                 345                 350

Cys Leu Ala Ser Leu Leu Ala Gln Tyr Ser Pro Glu His Leu Ala Gly
        355                 360                 365

Gln Arg Ile Ser Glu Phe Ser Tyr Gly Ser Gly Phe Ala Ala Thr Leu
    370                 375                 380

Tyr Ser Ile Arg Val Thr Gln Asp Ala Thr Pro Gly Ser Ala Leu Asp
385                 390                 395                 400

Lys Ile Thr Ala Ser Leu Ser Asp Leu Lys Ala Arg Leu Asp Ser Arg
                405                 410                 415

Lys Cys Ile Ala Pro Asp Val Phe Ala Glu Asn Met Lys Ile Arg Gln
                420                 425                 430

Glu Thr His His Leu Ala Asn Tyr Ile Pro Gln Cys Ser Val Glu Asp
            435                 440                 445

Leu Phe Glu Gly Thr Trp Tyr Leu Val Arg Val Asp Glu Lys His Arg
        450                 455                 460

Arg Thr Tyr Ala Arg Arg Pro Val Met Gly Asp Gly Pro Leu Glu Ala
465                 470                 475                 480
```

|         |         |         |         | Val 485 | His     | Pro     | Gly     | Ile     | Val 490 | His     | Glu     | His     | Ile     | Pro 495 | Ser     |
| Gly | Val | Glu | Val | | | | | | | | | | | | |
| Pro | Ala | Lys | Lys 500 | Val | Pro | Arg | Ile | Pro 505 | Ala | Thr | Thr | Glu | Ser 510 | Glu | Gly |
| Val | Thr | Val 515 | Ala | Ile | Ser | Asn | Gly 520 | Val | His | | | | | | |

( 2 ) INFORMATION FOR SEQ ID NO:3:

( i ) SEQUENCE CHARACTERISTICS:
( A ) LENGTH: 507 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

| Met 1 | Gln | Arg | Leu | Leu 5 | Ala | Pro | Ala | Arg | Val 10 | Leu | Gln | Val | Lys | Arg 15 |
|---|---|---|---|---|---|---|---|---|---|---|---|---|---|---|
| Val | Met | Gln | Glu 20 | Ser | Ser | Leu | Ser | Pro 25 | Ala | His | Leu | Leu | Pro 30 | Ala | Ala |
| Gln | Gln | Arg 35 | Phe | Ser | Thr | Ile | Pro 40 | Pro | Ala | Pro | Leu | Ala 45 | Lys | Thr | Asp |
| Thr | Trp 50 | Pro | Lys | Asp | Val | Gly 55 | Ile | Leu | Ala | Leu | Glu 60 | Val | Tyr | Phe | Pro |
| Ala 65 | Gln | Tyr | Val | Asp 70 | Gln | Thr | Asp | Leu | Glu 75 | Lys | Phe | Asn | Asn | Val 80 | Glu |
| Ala | Gly | Lys | Tyr | Thr 85 | Val | Gly | Leu | Gly | Gln 90 | Thr | Arg | Met | Gly | Phe 95 | Cys |
| Ser | Val | Gln | Glu 100 | Asp | Ile | Asn | Ser | Leu 105 | Cys | Leu | Thr | Val | Val 110 | Gln | Arg |
| Leu | Met | Glu | Arg 115 | Thr | Lys | Leu | Pro | Trp 120 | Asp | Ala | Val | Gly | Arg 125 | Leu | Glu |
| Val | Gly | Thr 130 | Glu | Thr | Ile | Ile 135 | Asp | Lys | Ser | Lys | Ala 140 | Val | Lys | Thr | Val |
| Leu 145 | Met | Glu | Leu | Phe | Gln 150 | Asp | Ser | Gly | Asn | Thr 155 | Asp | Ile | Glu | Gly | Ile 160 |
| Asp | Thr | Thr | Asn | Ala 165 | Cys | Tyr | Gly | Gly | Thr 170 | Ala | Ser | Leu | Phe | Asn 175 | Ala |
| Ala | Asn | Trp | Met 180 | Glu | Ser | Ser | Tyr | Trp 185 | Asp | Gly | Arg | Tyr | Ala 190 | Leu | Val |
| Val | Cys | Gly 195 | Asp | Ile | Ala | Val | Tyr 200 | Pro | Ser | Gly | Asn | Pro 205 | Arg | Pro | Thr |
| Gly | Gly 210 | Ala | Gly | Ala | Val | Ala 215 | Met | Leu | Ile | Gly | Pro 220 | Lys | Ala | Pro | Leu |
| Val 225 | Leu | Glu | Gln | Gly | Leu 230 | Arg | Gly | Thr | His | Met 235 | Glu | Asn | Ala | Tyr | Asp 240 |
| Phe | Tyr | Lys | Pro | Asn 245 | Leu | Ala | Ser | Glu | Tyr 250 | Pro | Leu | Val | Asp | Gly 255 | Lys |
| Leu | Ser | Ile | Gln 260 | Cys | Tyr | Leu | Arg | Ala 265 | Leu | Asp | Arg | Cys | Tyr 270 | Ala | Ala |
| Tyr | Arg | Arg 275 | Lys | Ile | Gln | Asn | Gln 280 | Trp | Lys | Gln | Ala | Gly 285 | Asn | Asn | Gln |
| Pro | Phe 290 | Thr | Leu | Asp | Asp | Val 295 | Gln | Tyr | Met | Ile | Phe 300 | His | Thr | Pro | Phe |
| Cys | Lys | Met | Val | Gln | Lys | Ser | Leu | Ala | Arg | Leu | Met | Phe | Asn | Asp | Phe |

|   |   |   |   | 305 |   |   |   |   | 310 |   |   |   |   | 315 |   |   |   |   | 320 |
|---|---|---|---|---|---|---|---|---|---|---|---|---|---|---|---|---|---|---|---|

Leu Ser Ser Ser Ser Asp Lys Gln Asn Asn Leu Tyr Lys Gly Leu Glu
              325             330             335

Ala Phe Lys Gly Leu Lys Leu Glu Glu Thr Tyr Thr Asn Lys Asp Val
            340             345             350

Asp Lys Ala Leu Leu Lys Ala Ser Leu Asp Met Phe Asn Lys Lys Thr
            355             360             365

Lys Ala Ser Leu Tyr Leu Ser Thr Asn Asn Gly Asn Met Tyr Thr Ser
    370             375             380

Ser Leu Gly Cys Leu Ala Ser Leu Leu Ser His His Ser Ala Gln Glu
385             390             395             400

Leu Ala Gly Ser Arg Ile Gly Ala Phe Ser Tyr Gly Ser Gly Leu Ala
                405             410             415

Ala Ser Phe Phe Ser Phe Arg Val Ser Lys Asp Ala Ser Pro Gly Ser
            420             425             430

Pro Leu Glu Lys Leu Val Ser Ser Val Ser Asp Leu Pro Lys Arg Leu
            435             440             445

Asp Ser Arg Arg Arg Met Ser Pro Glu Glu Phe Thr Glu Ile Met Asn
    450             455             460

Gln Arg Glu Gln Phe Tyr His Lys Val Asn Phe Ser Pro Pro Gly Asp
465             470             475             480

Thr Ser Asn Leu Phe Pro Gly Thr Trp Tyr Leu Glu Arg Val Asp Glu
                485             490             495

Met His Arg Arg Lys Tyr Ala Arg Arg Pro Val
                500             505

(2) INFORMATION FOR SEQ ID NO:4:

(i) SEQUENCE CHARACTERISTICS:
        (A) LENGTH: 520 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Pro Gly Ser Leu Pro Leu Asn Ala Glu Ala Cys Trp Pro Lys Asp
1               5               10              15

Val Gly Ile Val Ala Leu Glu Ile Tyr Phe Pro Ser Gln Tyr Val Asp
            20              25              30

Gln Ala Glu Leu Glu Lys Tyr Asp Gly Val Asp Ala Gly Lys Tyr Thr
            35              40              45

Ile Gly Leu Gly Gln Ala Arg Met Gly Phe Cys Thr Asp Arg Glu Asp
    50              55              60

Ile Asn Ser Leu Cys Leu Thr Val Val Gln Asn Leu Met Glu Arg Asn
65              70              75              80

Ser Leu Ser Tyr Asp Cys Ile Gly Arg Leu Glu Val Gly Thr Glu Thr
            85              90              95

Ile Ile Asp Lys Ser Lys Ser Val Lys Ser Asn Leu Met Gln Leu Phe
            100             105             110

Glu Glu Ser Gly Asn Thr Asp Ile Glu Gly Ile Asp Thr Thr Asn Ala
            115             120             125

Cys Tyr Gly Gly Thr Ala Ala Val Phe Asn Ala Val Asn Trp Ile Glu
    130             135             140

Ser Ser Ser Trp Asp Gly Arg Tyr Ala Leu Val Val Ala Gly Asp Ile
145             150             155             160

```
Ala Ile Tyr Ala Thr Gly Asn Ala Arg Pro Thr Gly Gly Val Gly Ala
            165                 170                 175
Val Ala Leu Leu Ile Gly Pro Asn Ala Pro Leu Ile Phe Asp Arg Gly
            180                 185                 190
Leu Arg Gly Thr His Met Gln His Ala Tyr Asp Phe Tyr Lys Pro Asp
            195                 200                 205
Met Leu Ser Glu Tyr Pro Ile Val Asp Gly Lys Leu Ser Ile Gln Cys
    210                 215                 220
Tyr Leu Ser Ala Leu Asp Arg Cys Tyr Ser Val Tyr Arg Lys Lys Ile
225                 230                 235                 240
Arg Ala Gln Trp Gln Lys Glu Gly Asn Asp Asn Asp Phe Thr Leu Asn
                245                 250                 255
Asp Phe Gly Phe Met Ile Ser His Ser Pro Tyr Cys Lys Leu Val Gln
            260                 265                 270
Lys Ser Leu Ala Arg Met Phe Leu Asn Asp Phe Leu Asn Asp Gln Asn
    275                 280                 285
Arg Asp Lys Asn Ser Ile Tyr Ser Gly Leu Glu Ala Phe Gly Asp Val
    290                 295                 300
Lys Leu Glu Asp Thr Tyr Phe Asp Arg Asp Val Glu Lys Ala Phe Met
305                 310                 315                 320
Lys Ala Ser Ser Glu Leu Phe Asn Gln Lys Thr Lys Ala Ser Leu Leu
                325                 330                 335
Val Ser Asn Gln Asn Gly Asn Met Tyr Thr Ser Ser Val Tyr Gly Ser
            340                 345                 350
Leu Ala Ser Val Leu Ala Gln Tyr Ser Pro Gln Gln Leu Ala Gly Lys
            355                 360                 365
Arg Ile Gly Val Phe Ser Tyr Gly Ser Gly Leu Ala Ala Thr Leu Tyr
    370                 375                 380
Ser Leu Lys Val Thr Gln Asp Ala Thr Pro Gly Ser Ala Leu Asp Lys
385                 390                 395                 400
Val Thr Ala Ser Leu Cys Asp Leu Lys Ser Arg Leu Asp Ser Arg Thr
                405                 410                 415
Cys Val Ala Pro Asp Val Phe Ala Glu Asn Met Lys Leu Arg Glu Asp
            420                 425                 430
Thr His His Leu Ala Asn Tyr Ile Pro Gln Cys Ser Ile Asp Ser Leu
    435                 440                 445
Phe Glu Gly Thr Trp Tyr Leu Val Arg Val Asp Glu Lys His Arg Arg
    450                 455                 460
Thr Tyr Ala Arg Arg Pro Ser Thr Asn Asp His Asn Leu Gly Asp Gly
465                 470                 475                 480
Val Gly Leu Val His Ser Asn Thr Ala Thr Glu His Ile Pro Ser Pro
                485                 490                 495
Ala Lys Lys Val Pro Arg Leu Pro Ala Thr Ala Ala Glu Ser Glu Ser
            500                 505                 510
Ala Val Ile Ser Asn Gly Glu His
            515                 520
```

( 2 ) INFORMATION FOR SEQ ID NO:5:

( i ) SEQUENCE CHARACTERISTICS:
        ( A ) LENGTH: 520 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met<br>1 | Pro | Gly | Ser | Leu<br>5 | Pro | Leu | Asn | Ala<br>10 | Ala | Cys | Trp | Pro | Lys<br>15 | Asp |
| Val | Gly | Ile | Val<br>20 | Ala | Leu | Glu | Ile<br>25 | Tyr | Phe | Pro | Ser | Gln<br>30 | Tyr | Val | Asp |
| Gln | Ala | Glu<br>35 | Leu | Glu | Lys | Tyr | Asp<br>40 | Gly | Val | Asp | Ala | Gly<br>45 | Lys | Tyr | Thr |
| Ile | Gly<br>50 | Leu | Gly | Gln | Ala | Arg<br>55 | Met | Gly | Phe | Cys | Thr<br>60 | Asp | Arg | Glu | Asp |
| Ile<br>65 | Asn | Ser | Leu | Cys | Leu<br>70 | Thr | Val | Val | Gln | Lys<br>75 | Leu | Met | Glu | Arg | Asn<br>80 |
| Ser | Leu | Ser | Tyr | Asp<br>85 | Cys | Ile | Gly | Arg | Leu<br>90 | Glu | Val | Gly | Thr | Glu<br>95 | Thr |
| Ile | Ile | Asp | Lys<br>100 | Ser | Lys | Ser | Val | Lys<br>105 | Ser | Asn | Leu | Met | Gln<br>110 | Leu | Phe |
| Glu | Glu | Ser<br>115 | Gly | Asn | Thr | Asp | Ile<br>120 | Glu | Gly | Ile | Asp | Thr<br>125 | Thr | Asn | Ala |
| Cys | Tyr<br>130 | Gly | Gly | Thr | Ala | Ala<br>135 | Val | Phe | Asn | Ala | Val<br>140 | Asn | Trp | Ile | Glu |
| Ser<br>145 | Ser | Ser | Trp | Asp | Gly<br>150 | Arg | Tyr | Ala | Leu | Val<br>155 | Val | Ala | Gly | Asp | Ile<br>160 |
| Ala | Ile | Tyr | Ala | Ser<br>165 | Gly | Asn | Ala | Arg | Pro<br>170 | Thr | Gly | Gly | Val | Gly<br>175 | Ala |
| Val | Ala | Leu | Leu<br>180 | Ile | Gly | Pro | Asn | Ala<br>185 | Pro | Val | Ile | Phe | Asp<br>190 | Arg | Gly |
| Leu | Arg | Gly<br>195 | Thr | His | Met | Gln | His<br>200 | Ala | Tyr | Asp | Phe | Tyr<br>205 | Lys | Pro | Asp |
| Met | Leu<br>210 | Ser | Glu | Tyr | Pro | Val<br>215 | Val | Asp | Gly | Lys | Leu<br>220 | Ser | Ile | Gln | Cys |
| Tyr<br>225 | Leu | Ser | Ala | Leu | Asp<br>230 | Arg | Cys | Tyr | Ser | Val<br>235 | Tyr | Arg | Lys | Lys | Ile<br>240 |
| Arg | Ala | Gln | Trp | Gln<br>245 | Lys | Glu | Gly | Lys | Asp<br>250 | Lys | Asp | Phe | Thr | Leu<br>255 | Asn |
| Asp | Phe | Gly | Phe<br>260 | Met | Ile | Phe | His | Ser<br>265 | Pro | Tyr | Cys | Lys | Leu<br>270 | Val | Gln |
| Lys | Ser | Leu<br>275 | Ala | Arg | Met | Phe | Leu<br>280 | Asn | Asp | Phe | Leu | Asn<br>285 | Asp | Gln | Asn |
| Arg | Asp<br>290 | Lys | Asn | Ser | Ile | Tyr<br>295 | Ser | Gly | Leu | Glu | Ala<br>300 | Phe | Gly | Asp | Val |
| Lys<br>305 | Leu | Glu | Asp | Thr | Tyr<br>310 | Phe | Asp | Arg | Asp | Val<br>315 | Glu | Lys | Ala | Phe | Met<br>320 |
| Lys | Ala | Ser | Ala | Glu<br>325 | Leu | Phe | Asn | Gln | Lys<br>330 | Thr | Lys | Ala | Ser | Leu<br>335 | Leu |
| Val | Ser | Asn | Gln<br>340 | Asn | Gly | Asn | Met | Tyr<br>345 | Thr | Ser | Ser | Val | Tyr<br>350 | Gly | Ser |
| Leu | Ala | Ser<br>355 | Val | Leu | Ala | Gln | Tyr<br>360 | Ser | Pro | Gln | Gln | Leu<br>365 | Ala | Gly | Lys |
| Arg | Ile<br>370 | Gly | Val | Phe | Ser | Tyr<br>375 | Gly | Ser | Gly | Leu | Ala<br>380 | Ala | Thr | Leu | Tyr |
| Ser<br>385 | Leu | Lys | Val | Thr | Gln<br>390 | Asp | Ala | Thr | Pro | Gly<br>395 | Ser | Ala | Leu | Asp | Lys<br>400 |
| Ile | Thr | Ala | Ser | Leu<br>405 | Cys | Asp | Leu | Lys | Ser<br>410 | Arg | Leu | Asp | Ser | Arg<br>415 | Thr |

```
Cys Val Ala Pro Asp Val Phe Ala Glu Asn Met Lys Leu Arg Glu Asp
            420             425             430

Thr His His Leu Ala Asn Tyr Ile Pro Gln Cys Ser Ile Asp Ser Leu
        435             440             445

Phe Glu Gly Thr Trp Tyr Leu Val Arg Val Asp Glu Lys His Arg Arg
    450             455             460

Thr Tyr Ala Arg Arg Pro Ser Thr Asn Asp His Ser Leu Asp Glu Gly
465             470             475             480

Val Gly Leu Val His Ser Asn Thr Ala Thr Glu His Ile Pro Ser Pro
                485             490             495

Ala Lys Lys Val Pro Arg Leu Pro Ala Thr Ser Gly Glu Pro Glu Ser
            500             505             510

Ala Val Ile Ser Asn Gly Glu His
            515             520
```

( 2 ) INFORMATION FOR SEQ ID NO:6:

( i ) SEQUENCE CHARACTERISTICS:
        ( A ) LENGTH: 520 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met Pro Gly Ser Leu Pro Leu Asn Ala Glu Ala Cys Trp Pro Lys Asp
1               5               10              15

Val Gly Ile Val Ala Leu Glu Ile Tyr Phe Pro Ser Gln Tyr Val Asp
            20              25              30

Gln Ala Glu Leu Glu Lys Tyr Asp Gly Val Asp Ala Gly Lys Tyr Thr
        35              40              45

Ile Gly Leu Gly Gln Ala Lys Met Gly Phe Cys Thr Asp Arg Glu Asp
    50              55              60

Ile Asn Ser Leu Cys Met Thr Val Val Gln Asn Leu Met Glu Arg Asn
65              70              75              80

Asn Leu Ser Tyr Asp Cys Ile Gly Arg Leu Glu Val Gly Thr Glu Thr
            85              90              95

Ile Ile Asp Lys Ser Lys Ser Val Lys Thr Asn Leu Met Gln Leu Phe
            100             105             110

Glu Glu Ser Gly Asn Thr Asp Ile Glu Gly Ile Asp Thr Thr Asn Ala
        115             120             125

Cys Tyr Gly Gly Thr Ala Ala Val Phe Asn Ala Val Asn Trp Ile Glu
    130             135             140

Ser Ser Ser Trp Asp Gly Arg Tyr Ala Leu Val Val Ala Gly Asp Ile
145             150             155             160

Ala Val Tyr Ala Thr Gly Asn Ala Arg Pro Thr Gly Gly Val Gly Ala
            165             170             175

Val Ala Leu Leu Ile Gly Pro Asn Ala Pro Leu Ile Phe Glu Arg Gly
            180             185             190

Leu Arg Gly Thr His Met Gln His Ala Tyr Asp Phe Tyr Lys Pro Asp
        195             200             205

Met Leu Ser Glu Tyr Pro Ile Val Asp Gly Lys Leu Ser Ile Gln Cys
    210             215             220

Tyr Leu Ser Ala Leu Asp Arg Cys Tyr Ser Val Tyr Cys Lys Lys Ile
225             230             235             240
```

```
His Ala Gln Trp Gln Lys Glu Ala Asn Asp Asn Asp Phe Thr Leu Asn
            245             250                     255

Asp Phe Gly Phe Met Ile Phe His Ser Pro Tyr Cys Lys Leu Val Gln
            260             265                     270

Lys Ser Leu Ala Arg Met Leu Leu Asn Asp Phe Leu Asn Asp Gln Asn
        275             280                 285

Arg Asp Lys Asn Ser Ile Tyr Ser Gly Leu Lys Ala Phe Gly Asp Val
    290             295                 300

Lys Leu Glu Asp Thr Tyr Phe Asp Arg Asp Val Glu Lys Ala Phe Met
305             310             315                         320

Lys Ala Ser Ser Glu Leu Phe Ser Gln Lys Thr Lys Ala Ser Leu Leu
            325             330                     335

Val Ser Asn Gln Asn Gly Asn Met Tyr Thr Ser Ser Val Tyr Gly Ser
            340             345                     350

Leu Ala Ser Val Leu Ala Gln Tyr Ser Pro Gln His Leu Ala Gly Lys
        355             360                 365

Arg Ile Gly Val Phe Ser Tyr Gly Ser Gly Leu Ala Ala Thr Leu Tyr
    370             375                 380

Ser Leu Lys Val Thr Gln Asp Ala Thr Pro Gly Ser Ala Leu Asp Lys
385             390             395                         400

Ile Thr Ala Ser Leu Cys Asp Leu Lys Ser Arg Leu Asp Ser Arg Thr
            405             410                     415

Gly Val Ala Gln Asp Val Phe Ala Glu Asn Met Lys Leu Arg Glu Asp
            420             425                     430

Thr His His Leu Val Asn Tyr Ile Pro Gln Gly Ser Ile Asp Ser Leu
        435             440                 445

Phe Glu Gly Thr Trp Tyr Leu Val Arg Val Asp Glu Lys His Arg Arg
    450             455                 460

Thr Tyr Ala Arg Arg Pro Thr Pro Asn Asp Asp Thr Leu Asp Glu Gly
465             470             475                         480

Val Gly Leu Val His Ser Asn Ile Ala Thr Glu His Ile Pro Ser Pro
            485             490                     495

Ala Lys Lys Val Pro Arg Leu Pro Ala Thr Ala Ala Glu Pro Glu Ala
            500             505                     510

Ala Val Ile Ser Asn Gly Val Trp
        515             520
```

3-HYDROXY-3-METHYL-GLUTARYL-COA SYNTHASE PREPARATION WITH IMPROVED STABILITY

This application is a continuation of application Ser. No. 08/072,040, filed Jun. 2, 1993, now abandoned.

FIELD OF THE INVENTION

The present invention relates to enzyme purification and storage. More specifically, the present invention relates to a recombinant 3-hydroxy-3-methylglutaryl-CoA synthase preparation with high specific activity that lacks substantial proteolytic cleavage, is stable during long-term 4° C. storage and is suitable as a reagent in assays for evaluating anti-cholesterol and anti-isoprene agents.

BACKGROUND

3-Hydroxy-3-methylglutaryl-CoA (HMG-CoA) synthase (E.C. 4.1.3.5) catalyzes the formation of a key intermediate in the cholesterogenic and ketogenic pathways in a three step process (Miziorko, et al., (1977) J. Biol. Chem. 252, 1414–1420):

(1) EnzSH+acetyl-CoA→acetyl-SEnz+CoASH (2) acetoacetyl-CoA+acetyl-SEnz→EnzS-HMG-CoA (3) EnzS-HMG-CoA+$H_2O$→EnzSH+HMG-CoA Distinct hepatic isozymes catalyze the synthesis of cholesterogenic and ketogenic intermediates (Clinkenbeard et al., (1975) J. Biol. Chem. 250, 3124–3135). As anticipated for the enzyme that catalyzes the first irreversible step in these metabolic pathways, HMG-CoA synthase has been implicated as a control point (Smith et al., (1988) J. Biol. Chem. 263, 18480–18487; Casals et al., (1992) Biochem. J. 283, 261–264; Quant et al., (1989) Biochem. J. 262, 159–164). These observations account for the recent interest in developing anti-steroidogenic and anti-isoprenyl agents that selectively target this enzyme (Omura et al., (1987) J. Antibiotics 40, 1356–1357).

Elements of the active site of this important enzyme have been identified (Miziorko, et al. (1985) Biochemistry 24, 3174–3179; Miziorko, et al., (1985) J. Biol. Chem. 260, 13513–13516; Vollmer et al., (1988) Biochemistry 27, 4288–4292; Miziorko et al., (1990) Biochim. Biophys. Acta 1041, 273278) in studies that relied on synthase isolated from an avian source. These synthase preparations have particular characteristics that render their use in drug targeting studies problematic. For example, an avian liver cytosolic synthase (Clinkenbeard, et al., 1975, supra) was found to be proteolytically cleaved. This would account for the differences in molecular weight, isoelectric point, and chromatographic properties that were observed for four different putative cytosolic protein species that, upon isolation, were found to catalyze the formation of HMG-CoA. Miziorko ((1985) *Methods of Enzymology* 110, p. 19–26, Ed. J. H. Law and Hans C. Rilling) noted that a crude preparation of HMG-CoA synthase isolated from chicken liver had only 20% activity after storage at 4° C. for 24 hours.

HMG-CoA synthase is used to assay drugs believed to be efficacious in cholesterol reduction because of the pivotal role the synthase plays in the production of cholesterol. Similarly, one could use HMG-CoA synthase preparations to assay drugs thought to be capable of inhibiting isoprenylation of proteins, which may be a step in cancer metabolism. Investigation of putative anti-cholesterol and anti-isoprene drugs is handicapped by the quality of prior art native HMG-CoA synthase preparations. Additional investigation of synthase properties could be facilitated by application of recombinant DNA methodology to allow more convenient production of the enzyme and engineered variants. We previously documented the isolation of full length cDNA encoding avian liver HMG-CoA synthase (Kattar-Cooley et al., (1990) Arch. Biochem. Biophys. 283, 523–529). The genes for the rat mitochondrial and cytosolic HMG-CoA synthase have been analyzed by Ayte. et al., (1990, Proc. Natl. Acad. Sci. U.S.A. 87, 3874–3878). These workers expressed cDNA clones of the synthase gene in *E. coli* with a resulting specific activity of between 0.4 and 1.2 milliunits/mg. Hamster HMG-CoA synthase was cloned by Gil, et al. (Gil, et al., 1986, J. Biol. Chem. 261, 3710–3716.).

SUMMARY OF THE INVENTION

The present invention is a preparation of recombinant HMG-CoA synthase with improved stability properties. In one embodiment of the invention, the preparation has at least 0.024 units/mg specific activity. Preferably, the preparation has at least 0.240 units/mg specific activity and is a crude cell extract. In a preferred form, at least 90% of the synthase molecules have not been substantially proteolytically cleaved. By "substantially proteolytically cleaved", we mean that only the initial methionine of the protein is cleaved and the rest of the protein is intact.

In another embodiment, the present invention is a preparation of recombinant HMG-CoA synthase retaining 50% activity after storage at 4° C. for six months. Preferably, this preparation retains 50% activity after storage at one year at 4° C.

In another embodiment, the present invention is a method for analyzing the efficacy of anti-cholesterol or anti-isoprene drugs, comprising the step of exposing the candidate drug to the preparations of HMG-CoA synthase disclosed above.

It is an advantage of the present invention that an HMG-CoA synthase preparation with improved stability qualities is provided.

Another advantage of the present invention is that a preparation yielding sufficient amounts and quality of HMG-CoA synthase to more effectively analyze anti-cholesterol and anti-isoprene drugs is enabled.

Another advantage of the present invention is that a recombinant avian HMG-CoA synthase preparation with improved stability characteristics is provided.

Another advantage of the present invention is that a preparation of cytosolic HMG-CoA synthase with improved stability characteristics is provided.

It is a feature of the present invention that the HMG-CoA synthase preparation is at least 50% active after storage at 4° C. for six months.

It is another feature of the present invention that at least 90% of the preparation is not substantially proteolytically cleaved.

It is another feature of the present invention that a crude bacterial lysate extract of the synthase has at least 0.025 units/mg specific activity.

Other objects, features and advantages to the present invention will become apparent after examination of the specification, claims and drawings. The specification and drawings are not meant to limit the scope of the invention, but to provide specific embodiments. Only the claims of the present application are meant to limit the scope of the invention. Other embodiments of the invention are within the spirit and scope of the invention and will be apparent to one skilled in the art.

DESCRIPTION OF THE DRAWINGS

FIG. 1 is an amino acid comparison of five different HMG-CoA synthases. FIG. 1A encompasses the amino acid comparison between amino acid residues 1 and 300 and FIG. 1B comprises amino acid residues 301 to 560.

FIG. 2 is a schematic diagram of the construction of expression plasmid pACS encoding avian cytosolic HMG-CoA synthase.

DESCRIPTION OF THE PREFERRED EMBODIMENT

Figure 3:
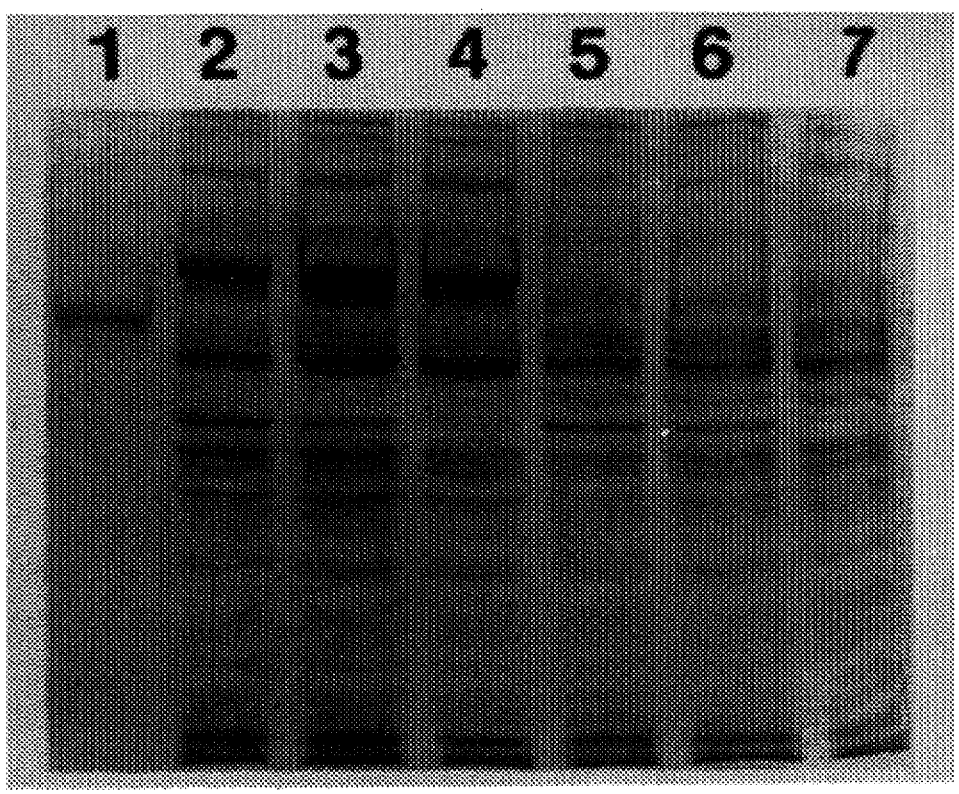
FIG. 3 is an electrophoretic gel demonstrating the expression of cytosolic HMG-CoA synthase in E. coli.

The present invention is a preparation of recombinant HMG-CoA synthase with improved stability characteristics. In one embodiment, a crude cell extract preparation has a specific activity of at least 0.024 units/mg, preferably a specific activity of at least 0.24 units/mg. By "crude cell extract" preparation we mean an enzyme preparation that has not been substantially purified from the host cell producing the enzyme. Also preferably, at least 90% of the molecules have not been substantially proteolytically cleaved. In another embodiment, the present invention is an HMG-CoA synthase preparation that retains at least 50% activity after storage at 4° C. for six months, preferably for one year.

The preparation of the present invention will be useful in studies evaluating drugs as anti-cholesterol and anti-isoprene agents. The improved stability of the preparation of the present invention will allow workers to perform these studies on a reliable, consistent protein preparation and make determination of the candidate drug's efficacy an easier task.

1. Creation of a Recombinant HMG-CoA Synthase Expression System

A nucleic acid sequence encoding HMG-CoA synthase is obtained and joined to appropriate regulatory sequences. A preferable sequence is disclosed in SEQ ID NO:1. The Examples below disclose how SEQ ID NO:1 was obtained from the avian cDNA clone described in Kattar-Cooley, et al., supra (hereby incorporated by reference). The first base (C) in SEQ ID NO:1 is a noncoding base added to furnish an Nco I site. The rest of the sequence is coding sequence up to nucleotide 1570. The nucleotides between 1571 and 1824 are noncoding sequences. The resulting sequence described in the Examples has the second amino acid (a proline in native HMG-CoA synthase) replaced by an alanine. The translation product of the avian cDNA is presented in SEQ ID NO:2.

To replicate SEQ ID NO:1, one would most easily start by obtaining an avian HMG-CoA cDNA clone. To obtain an avian HMG-CoA cDNA clone, one could use SEQ ID NO:1 to construct probes suitable for screening an avian cDNA library. Alternatively, one could construct primers for use in a polymerase chain reaction following synthesis of a DNA strand from avian messenger RNA using reverse transcription. Other methods will be known to one skilled in the art. One could then use method described in the Examples to manipulate the cDNA sequence.

Clones for HMG-CoA synthase have also been isolated from rat (mitochondrial and cytosolic), human, and hamster. The translation product for rat mitochondrial synthase is SEQ ID NO:3, for hamster synthase is SEQ ID NO:4, for rat cytosolic synthase is SEQ ID NO:5, and for human synthase is SEQ ID NO:6. (The rat mitochondrial sequence is disclosed in Ayte, et al., 1990, Natl. Acad. Sci., 87, 3874–3878; the rat cytosolic sequence is disclosed in Ayte, et al., 1990, Nucl. Acids Res., 18, 3642–3642; the hamster sequence is disclosed in Gil, et al., 1986, J. Biol. Chem., 261, 3710–3716; and the human sequence is disclosed in Russ, et al., 1992, Biochem. Biophys. Acta, 1132, 329–331.)

FIG. 1 compares the amino acid sequences of the different HMG-CoA synthases and demonstrates the homology between them. The sequences in FIG. 1 have the following legend: "Hmcs$Crigr" indicates the hamster sequence; "Hmcs$Rat" indicates the rat cytosolic sequence; "Synthase" indicates the human sequence; "Avcytsyn" indicates the avian sequence and "Hmcm$Rat" indicates the rat mitochondrial sequence. In general, a high (>80%) degree of homology is observed between cytosolic HMG-CoA synthases. Comparison between cytosolic and mitochondrial isozymes shows lower (<70%) homology, even when the isozymes are derived from the same tissue.

Appropriate regulatory sequences must be added to the HMG-CoA synthase sequence for protein expression. The Examples below demonstrate suitable appropriate sequences for expression in an E. coli host. If another host is desired, such as yeast or animal cells, the art is knowledgeable about other appropriate regulatory sequences.

The recombinant protein produced by the host must then be isolated, preferably as described in the Examples, although other isolation techniques would be equally suitable. The protocol described in the Examples is analogous to the procedure for isolation of the homologously expressed avian protein. The purification protocol becomes less stringent as the percentage of total protein in crude extracts that is represented by HMG-CoA synthase increases.

When one constructs an expression system with an HMG-CoA synthase sequence, regulatory sequences and suitable host, it will then be necessary to examine the protein preparation for specific activity, proteolytic cleavage, and stability after 4° C. storage as described below and in the Examples.

2. Analysis of Recombinant HMG-CoA Synthase a. Measurement of Specific Activity

The synthase preparation of the present invention has a specific activity of at least 0.024 units/mg., preferably at least 0.24 units/mg. The Examples below disclose specific activity measurements during various stages of recombinant protein purification. A unit of synthase activity is defined as the amount of enzyme that will catalyze conversion of one micromole of each substrate (i.e. acetyl-CoA and acetoacetyl-CoA) to product HMG-CoA in one minute.

Miziorko, et al., 1975, supra (hereby incorporated by reference) discloses a preferable specific activity determination. This method is described fully in the Examples. In brief, the time dependent conversion of [$^{14}$C]acetyl-CoA to acid stable [$^{14}$C] HMG-CoA is measured. Alternately, a spectrophotometric approach can be used; this involves measurement of the time dependent decrease in ultraviolet absorbance due to acetoacetyl-CoA, as this substrate is converted (upon reaction with acetyl-CoA) to the product of the reaction, which is HMG-CoA.

b. Measurement of Proteolytic Cleavage

In a preferred form of the present invention, at least 90% of the recombinant synthase preparation has not been substantially proteolytically cleaved. By "not substantially proteolytically cleaved" we mean that only the initial met residue has been cleaved.

The level of proteolytic cleavage is most preferably measured by Edman degradation to determine the N-terminal sequence of protein chains in the enzyme preparation.

c. Measurement of Stability After 4° C. Storage

In a preferred form of the present invention, the synthase preparation is stable at long-term (6 month) 4° C. storage. Preferably, the preparation retains 50% activity after one year of 4° C. storage. The Examples below disclose preferred methods for determining enzyme activity.

3. Analysis of Anti-cholesterol or Anti-Isoprene Drugs

The present invention is also a method of analyzing candidate drugs for their efficacy as anti-cholesterol or anti-isoprene agents. This analysis involves an observation of the effect that the candidate drug has on an HMG-CoA synthase preparation and, therefore, a cholesterol or isoprene biosynthesis. A drug capable of inactivating or modifying the synthase preparation is a good candidate for further study as a drug useful to combat high cholesterol biosynthesis that could contribute to elevated serum cholesterol levels.

The literature contains examples of previous attempts to study the interaction of various drugs with HMG-CoA synthase. For example, Greenspan, et al. (1993, Biochem J. 289, 889–895) discloses the inhibition of HMG-CoA synthase and cholesterol biosynthesis by beta-lactone inhibitors and the binding of these inhibitors to the enzyme. These workers analyzed a partially purified preparation of rat liver cytosolic HMG-CoA synthase with beta-lactone L-659,699 and its radioactive derivative. After determining that the lactone affected the synthase, the workers also examined cultured HepG2 cells in their ability to incorporate acetate into sterols. They found that sterol biosynthesis in cultured HepG2 cells was rapidly restored upon removal of the compound from the medium.

In general, investigations such as the Greenspan, et al., 1993, supra, involve the exposure of an HMG-CoA synthase protein preparation to the candidate drug or agent and the observation of how that drug or agent interacts with the protein preparation. Activity measurements (such as those disclosed below in the Examples) can be used to assess whether or not the HMG-CoA synthase remains in an active state. Activity measurements in crude native cellular fractions may be problematic due to interference from other enzymes or metabolites. Straightforward estimates of whether a potential drug affects HMG-CoA synthase activity are facilitated by availability and used of isolated recombinant HMG-CoA synthase enzyme with increased stability.

EXAMPLES

The Examples below describe the isolation and characterization of HMG-CoA synthase expressed in *E. coli*. The quality of this recombinant enzyme preparation is evaluated by comparison of its properties with natively isolated avian liver enzyme. Such a comparison also demonstrated that the isolated avian cDNA encodes the cholesterogenic isozyme.

2. Experimental Procedures a. Materials

*E. coli* BL21(DE3) and pET-3d vector were purchased from Novagen (Madison, Wis.). *E. coli* DH5α were obtained from Bethesda Research Laboratory (Gaithersburg, Md.). Restriction enzymes, T4 DNA ligase and vent DNA polymerase were purchased from New England Biolabs (Beverly, Mass.). Sequenase and IPTG (isopropylthiogalactoside) were provided by United States Biochemicals (Cleveland, Ohio). R.(3-carboxy-2,2,5,5-tetramethyl-1-pyrrolidinyloxyl;3-carboxy-PROXYL) was obtained from Aldrich (Milwaukee, Wis.). R.CoA thioester was synthesized using the mixed anhydride, prepared by activation of the free acid using the method of Bernert, et al., (1977) J. Biol. Chem. 252, 6736–6744. Deoxyoligonucleotides were synthesized by the Protein/Nucleic Acid Facility at the Medical College of Wisconsin. Geneclean is a product of Bio 101 Inc. (Vista, Calif.). All other reagents were purchased from Sigma Chemical Company (St. Louis, Mo.), Pharmacia (Milwaukee, Wis.) or Bio-Rad (Richmond, Calif.). Antiserum against rat cytosolic synthase was kindly provided by Dr. Michael Greenspan (Merck, Sharpe, & Dohme; Rahway, N.J.).

b. Methods

Construction of the Expression Vector. Isolation of full length cDNA encoding avian HMG-CoA synthase from a λgt11 library has been reported (Kattar-Cooley et al., supra, 1990). The cDNA encoding the synthase was derived from EcoRI insert of the λ clone NC9, subcloned into pUC13 (pKC5). FIG. 2 describes the cloning of the synthase cDNA into an *E. coli* expression vector. The ATG codon within the Nco I recognition site is in frame and functions as the translation initiation codon, encoding a methionine as residue 1. In this expression construct, alanine replaces a non-conserved proline as residue 2. The open, filled, and stippled segments in FIG. 2 represent the coding sequence, untranslated region, and ampicill in resistance gene, respectively. Linkers are represented by striped regions.

Referring to FIG. 2, after endonucleolytic digestion with SmaI and EcoRI, the 3'-terminus of SmaI-EcoRI insert was filled in with the Klenow fragment of DNA polymerase. Decameric linkers bearing an NcoI recognition sequence were ligated to the blunt-ended insert. The resulting fragment was purified and restricted with NcoI endonuclease to facilitate ligation (Maniatis et al., (1982) *Molecular Cloning*, Cold Spring Harbor, N.Y. pp. 1.53–1.72) into the NcoI cloning site of the expression vector pET-3d. The ligation mix was used to transform DH5α competent cells (Hanahan et al., (1991) *Methods Enzymol.*, 204, 63–113). Clones containing the insert in the desired orientation (as verified by restriction mapping) were isolated (Birnboim, et al., (1979) Nucleic Acid Res., 7, 1513–1523) and the DNA sequence encoding the N-terminus of the expression target was confirmed by dideoxy chain termination method (Sanger et al., (1977) Proc. Natl. Acad. Sci. USA 74, 5463–5467). *E. coli* BL21(DE3) cells were transformed with the purified plasmid pACS for HMG-CoA synthase expression.

Bacterial Growth and Purification of HMG-CoA Synthase. A single colony of *E. coli* BL21(DE3) harboring the recombinant plasmid was grown to stationary phase in LB media (Miller, (1972) *Experiments in Molecular Genetics*, Cold Spring Harbor, N.Y. pp. 431–435) containing 200 µg/ml ampicillin. The culture was diluted (1:100) with 3 liters of media of the same composition and grown at 30° C. on a gyrotory shaker. Expression was induced by addition of 1 mM IPTG to culture at an O.D. of 0.6–0.8. The cells were subsequently harvested by low speed centrifugation after the culture reached an O.D. of 2.2. The pellet was resuspended in lysis buffer (20 mM sodium phosphate pH 7.0, 1 mM EDTA, 1 mM DTT, 0.1 mM PMSF, 10% glycerol) and lysed in a French pressure cell at 16,000 psi. Supernatant was recovered from the crude extract by centrifugation at 46,000×g for 45 minutes.

HMG-CoA synthase was purified from the supernatant by an adaptation of the procedure of Clinkenbeard et al., (supra). An ammonium sulfate fraction (30–45% saturation), prepared from the supernatant, was dissolved in 20 mM sodium phosphate buffer pH 6.5, 0.1 mM EDTA, 0.1 mM DTT and dialyzed overnight against 20 liters of buffer of the same composition. The dialysate was loaded onto a 2.5×64 cm DEAE-cellulose column equilibrated with 20 mM sodium phosphate buffer, pH 6.5, containing 0.1 mM EDTA, and 0.1 mM DTT. The column was washed with 2 column volumes of the equilibration buffer and eluted using 1.6 liters of a 20–160 mM linear gradient of sodium phosphate buffer, pH 6.5, containing 0.1 mM EDTA and 0.1 mM DTT. The fractions containing HMG-CoA synthase activity were pooled and concentrated using an Amicon ultrafiltration cell. 100–150 mg of enzyme was isolated from a 3 liter culture.

Western Blotting. Methodology reported by Haas, et al., (1985, J. Biol. Chem., 260, 12464–12473), was employed for immunochemical detection of HMG-CoA synthase. Crude E. coli extract was electrophoresed on an SDS-polyacrylamide gel. The proteins were transferred to a nitrocellulose membrane, followed by incubation with a 1:1000 dilution of antiserum raised against avian mitochondrial synthase or rat cytosolic synthase and subsequent washing to eliminate non-specific binding. The resulting complex was visualized by incubation with a solution of [$^{125}$I] protein A, followed by autoradiography.

Characterization of the Recombinant Enzyme. For measurement of the overall condensation reaction (Miziorko et al., (1975) J. Biol. Chem. 250, 5678–5773), 200 µM acetyl-CoA was added to a reaction mixture (30° C.) containing 100 mM Tris-HCl pH 8.2, 100 µM EDTA, 50 µM acetoacetyl-CoA and appropriately diluted HMG-CoA synthase (approximately 6 µg wild type enzyme in 1.0 ml final volume). The reaction rate was monitored by acetyl-CoA dependant loss of absorbance at 300 nm, due to condensation with the enolate of acetoacetyl-CoA.

The enzyme's specific activity was calculated as µmoles/min/mg. (This is equivalent to units/mg, since 1 unit=1 umole/min.) Apparent $K_m$ measurement was done in the presence of 20 µM acetoacetylCoA. The enzyme's acetyl-CoA hydrolase activity was determined (Miziorko et al., 1975, supra) by measuring the time dependent depletion of [$^{14}$C]acetyl-CoA, after its conversion to acid stable citrate upon reaction with excess citrate synthase and oxaloacetate. The reaction mixture contained 100 mM potassium phosphate, pH 8.0, and 60 µg HMG-CoA synthase in 300 µl total volume at 30° C. The reaction was initiated by addition of 100 µM [$^{14}$C] acetyl-CoA (10,000 dpm/nmole). At specific time intervals, 20 µl aliquots were removed and added rapidly to a mixture containing 500 milliunits of citrate synthase and 400 µM oxaloacetate in 100 mM potassium phosphate buffer, pH 8.0 (100 µl final volume). The resulting mix was acidified with 100 µl of 6N HCl and heated to dryness. The acid stable radioactivity which is measured is due to unhydrolyzed [$^{14}$C] acetyl-CoA.

The stoichiometry of acetyl-CoA binding was determined according to the procedure of Vollmer et al. (1988, supra). After 30° C. incubation of the enzyme (120 µg) in 100 mM sodium phosphate, pH 7.5, the mixture was placed on ice. [$^{14}$C]acetyl-CoA (10,000 dpm/nmole) was added to bring the 100 µl incubation mixture to a final concentration of 200 µM. Unbound acetyl CoA was removed using a G-50 centrifugal column equilibrated with 10 mM sodium acetate, pH 5.0, at 4° C. Protein in the recovered samples was estimated by the Bradford assay ((1976) Anal. Biochem., 72, 248–254) and radioactivity was determined by liquid scintillation counting.

Stoichiometry of covalent acetylation was determined according to Miziorko et al. (1975, supra). The incubation mixture, containing [$^{14}$C]acetyl-CoA and 50 µg wild type or 300 µg mutant enzyme in 100 µl, was treated with 900 µl of ice-cold 10% trichloroacetic acid. The denatured protein was recovered by centrifugation. The pellet was resuspended in 10% trichloroacetic acid and transferred to a glass fiber filter. The filters were washed extensively with ice-cold 10% trichloroacetic acid and 50 mM sodium pyrophosphate in 500 mM HCl, and once with cold absolute ethanol. Filters were dried and radioactivity was determined by liquid scintillation counting.

Measurement of R.CoA Binding by EPR. Conventional X-band EPR spectra were recorded using a Varian Century-Line 9-GHz spectrometer. The samples contained variable concentrations of HMG-CoA synthase sites (0–930 µM) in 50 mM sodium phosphate buffer, pH 7.0, and 50 or 150 µM R.CoA. R.CoA bound to HMG-CoA synthase was calculated by comparing the amplitudes of high, center, or low-field lines of sample spectra to the corresponding lines observed with a solution containing an equal concentration of R.CoA in buffer. The data were analyzed (Miziorko et al., (1979) Biochemistry 18, 399–403) by Scatchard plot using linear regression analysis. The spectra were recorded at ambient temperature with a modulation amplitude of 1 G, modulation frequency of 100 KHz and microwave power 5 mW. Field sweep was 100 G and time constant was 0.5 sec. The EPR spectrum of bound R.CoA was obtained at 5 G modulation amplitude and variable gain. Rotational correlation time of the bound spin label was determined using a spectral simulation algorithm (Freed, (1976) Spin Labeling: Theory and Applications (L. Berliner, ed.) 1, 53–132; Schneider, et al. (1989) Biological Magnetic Resonance 8, 1–76).

Measurement of Proteolytic Cleavage. Evaluation of the degree of proteolysis of the recombinant HMG-CoA synthase was based on N-terminal sequence analysis by the Edman degradation procedure. Typically >100 picomoles of protein are used for analysis, which was carried out using an Applied Biosystems model 477A pulsed liquid phase sequencer equipped with online PTH analyzer (Model 120) to detect the phenylthiohydatoin derivatives of amino acids released at each step in the analysis. Ten Edman cycles were usually sufficient to characterize the preparation.

3. Results

Expression and Isolation of Recombinant HMG-CoA Synthase. T7 polymerase-dependent protein synthesis was induced by addition of IPTG to the E. coli BL21(DE3) culture that has been transformed with expression plasmid pACS, which contains synthase-encoding cDNA. FIG. 3, a Coomassie-stained SDS-polyacrylamide gel, is a demonstration of the expression of cytosolic HMG-CoA synthase in E. coli. Lane 1 is the avian liver mitochondrial HMG-CoA synthase (2 micrograms); lanes 2, 3 and 4 are total extract, 46,000×g supernatant, and 10,000×g supernatant, respectively from E. coli harboring the expression plasmid (12 microgram protein); lanes 5, 6 and 7 are fractions equivalent to those described for lanes 2, 3 and 4, but are derived from bacterial cells carrying the vector plasmid only (12 micrograms protein). There was a marked accumulation of protein (FIG. 3, lane 2) which exhibits a subunit molecular weight in excess of that observed for a liver mitochondrial synthase marker (FIG. 3, lane 1). No comparable protein appeared upon addition of IPTG to bacteria containing only the parent pET-3d vector (FIG. 3, lanes 5–7). There is a 5 kDa increment in subunit molecular weight for the avian cytosolic HMG-CoA synthase (Clinkenbeard et al., 1975, supra) over that of the mature mitochondrial isozyme (Reed et al., (1975) J. Biol. Chem. 250, 3117–3123).

Appearance of this prominent Coomassie-stained band prompted activity assays which demonstrated high levels of HMG-CoA synthase activity in extracts of bacteria that harbor the expression plasmid and no activity in samples from bacteria containing the pET-3d vector. Table 1, below, summarizes these results. Based on the specific activity of purified synthase (vide infra), approximately 24% of protein in the crude bacterial extracts was attributable to the target of T7 polymerase dependent expression. Importantly, virtually all of the expressed protein is active and soluble, as judged from measurements on high speed supernatants (FIG. 3, lanes 3,4; Table 1).

TABLE 1

| Purification step | Total Protein (mg) | Total units | Specific Activity (Units/mg) | Purification (Fold) | Yield (%) |
|---|---|---|---|---|---|
| Crude Extract | 1,820 | 451 | 0.24 | (1) | (100) |
| High Speed Supernatant | 1,732 | 407 | 0.23 | 0.96 | 90 |
| 30–45% $(NH_4)_2SO_4$ Fractionation | 623 | 302 | 0.48 | 2.0 | 67 |
| DEAE-Cellulose Chromatography | 150 | 151 | 1.00 | 4.1 | 33 |

Figure 4:
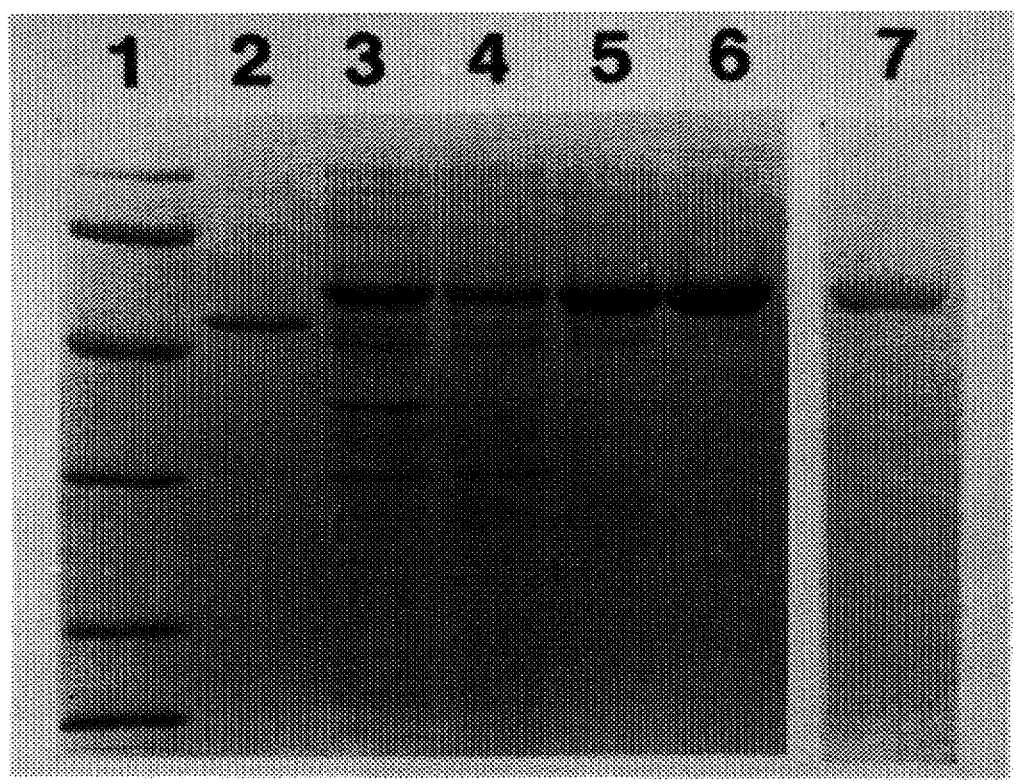
FIG. 4 is an electrophoretic gel of recombinant HMG-CoA synthase at various stages of purification.

The level of overexpression facilitated isolation of significant amounts of homogeneous enzyme by application of rudimentary salt fractionation and ion exchange chromatography procedures (FIG. 4; Table I). FIG. 4 is an SDS polyacrylamide electrophoretic gel containing recombinant HMG-CoA synthase. The samples correspond to the recombinant wild-type enzyme at various stage of purification (Lanes 3–6) and a modified recombinant HMG synthase in Lane 7. Lane 1 represents molecular weight markers (serum albumin, 66.2 kDa; ovalbumin, 45 kDa; carbonic anhydrase, 31 kDa; soybean trypsin inhibitor, 21.5 kDa; lysozyme, 14.4 kDa). Lane 2 is mitochondrial HMG-CoA synthase isolated from chicken liver. Lane 3 is total extract of E. coli containing the plasmid encoding wild-type HMG-CoA synthase (12 micrograms). Lane 4 is a supernatant (10 micrograms) obtained after centrifugation of bacterial extract at 46,000×g for 45 minutes. Lane 5 is the 30–45% $(NH_4)_2SO_4$ fraction (10 micrograms). Lane 6 is a DEAE eluate (10 micrograms). Lane 7 is a purified mutated recombinant HMG-CoA synthase.

Specific activity of the isolated recombinant synthase is in excellent agreement with the highest values reported for the avian liver cytosolic enzyme (Clinkenbeard et al., 1975, supra). Unlike that enzyme, which was vulnerable to proteolysis, expression of our construct in E. coli results in an enzyme that is quite stable in crude extracts, during isolation, and upon long term storage. We determined that the preparation in its final purified form had 50% activity after one year at 4° C. storage and negligible loss at −80° C. storage.

Properties of Recombinant HMG-CoA Synthase. Table 2, below, is a comparison of the characteristics of our recombinant HMG-CoA synthase and native avian liver HMG-CoA synthases. In addition to comparable catalytic activity in the overall condensation reaction to form HMG-CoA, the apparent Michaelis constant was in excellent agreement with that estimated for the liver enzyme. The stoichiometry with which the covalent the acetyl-S-enzyme intermediate was trapped on the recombinant enzyme (Table 2) was also in good agreement with the range of values observed using various avian liver preparations. In the absence of the second substrate, acetoacetyl-CoA, HMG-CoA synthase catalyzes hydrolysis of acetyl-CoA (Miziorko et al., 1975, supra). The recombinant enzyme also catalyzes this partial reaction, exhibiting a rate and Michaelis constant (Table 2) that are in good agreement with that earlier report. It had been previously established that avian HMG-CoA synthase specifically binds a spin-labeled substrate analog, R.CoA, as a competitive inhibitor with respect to acetyl-CoA (Miziorko et al., 1979, supra). When evaluated for interaction with recombinant enzyme, R.CoA was found to bind at a stoichiometry of 0.9/protomer and with a $K_d$=102 uM, in agreement with the values reported for the avian enzyme. Moreover, simulation of the spectral features of the immobilized spin-labeled acyl-CoA (Freed, 1976, supra; Schneider, et al., 1989, supra) suggested a rotational correlation time, $\tau_c$=35 nanoseconds, which agrees with the range of values estimated for the avian enzyme. This $\tau_c$ value for the bound spin-probe predicts, according to the Stokes-Einstein equation, virtually complete immobilization of the acyl group on a 115 Kda protein, in agreement with the dimeric nature of the native, avian enzyme.

TABLE 2

| Parameters | Liver Enzyme[a] | Recombinant Enzyme[b] |
|---|---|---|
| Specific Activity (µmol/min/mg) | 0.5–1.0 | 0.8–1.0 |
| $K_m$ AcCoA (Overall Rxn.; µM) | 300 | 270 |
| Acetylation stoichiometry (mol/mol subunit) | 0.50–0.75 | 0.62 |
| Effect of $MgCl_2$ on activity | 40% increase | 45% increase |
| Hydrolase Activity (µmol/min/mg) | $1.0 \times 10^{-2}$ | $1.8 \times 10^{-2}$ |
| $K_m$ AcCoA (Hydrolase Rxn.; uM) | 14 | 12 |

In the overall condensation reaction, $K_m$ is an apparent value, as the conventional assay is performed in presence of 20 µM acetoacetyl-CoA, which is slightly inhibitory.
[a]Data for the liver enzyme are taken from Clinkenbeard et al (1975) and Miziorko et al (1975).
[b]Data for recombinant synthase are from this report, employing methodology described in detail in experimental procedures.

Upon Edman degradation analysis (10 cycles) of the purified recombinant HMG-CoA synthase, we determined that 90% of protein chains lacked the N-terminal methionine that was encoded by the AUG start codon in the cDNA. This processing of the N-terminal methionine is commonplace in bacteria. Thus, these proteins have an N-terminal alanine, which was encoded by the second codon of the modified cDNA as engineered and ligated into pACS. The remaining 10% of the preparation can largely be attributed to protein chains from which the N-terminal methionine has not been processed. No indication of extensive proteolysis during isolation from bacterial extract of the recombinant HMG-CoA synthase was apparent by the stringent criterion represented in these N-terminal analyses.

Recombinant HMG-CoA Synthase Represents the Cholesterogenic Isozyme. The primary sequence of the protein, as deduced from avian cDNA sequence data, has been assigned to the cytosolic, cholesterogenic HMG-CoA synthase (Kattar-Cooley et al., 1990, supra). This evaluation was based on comparison between the deduced sequence and the empirically determined (Edman degradation) sequence of a series of peptides isolated from the mitochondrial, ketogenic enzyme. Availability of the isolated recombinant enzyme facilitates further tests of this assignment. In addition to the observation of the predicted increment in subunit molecular weight that distinguishes mitochondrial and recombinant enzymes (FIG. 4), further differences were apparent upon immunochemical analysis.

Figure 5A:
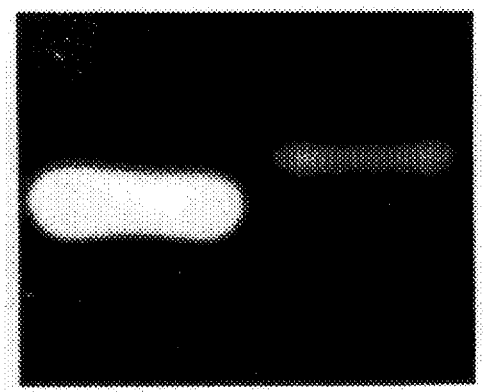
FIGS. 5A and B are a set of immunoblots prepared by reaction of HMG-CoA synthase samples with antiserum raised against avian mitochondrial HMG-CoA synthase (A) or rat cytosolic HMG-CoA synthase (B).

FIG. 5 is a set of immunoblots prepared by reaction of HMG-CoA synthase samples with antiserum raised against avian mitochondrial HMG-CoA synthase (A) or rat cytosolic HMG-CoA synthase (B). Lane 1 is avian liver mitochondrial HMG-CoA synthase (0.2 micrograms). Lane 2 is 2.5 micrograms of crude extract of IPTG-induced *E. coli* harboring the expression plasmid pACS. Antigen-antibody complexes are detected by autoradiography after reaction with [$^{125}$I] protein A. Panel B is intentionally overexposed to allow visualization of the weak cross-reaction between avian mitochondrial antigen and antiserum prepared against rat cytosolic antigen.

Figure 5B:
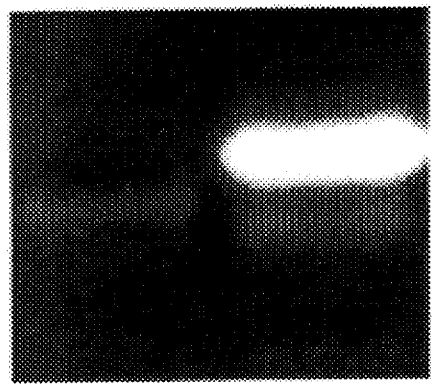

Referring to FIG. 5, in western blot experiments, antiserum prepared against isolated avian mitochondrial enzyme (Miziorko, 1985, supra) sensitively detected this antigen (FIG. 4a) as well as the recombinant synthase. However, when antiserum prepared against the rodent cytosolic, cholesterogenic synthase (Mehrabian et al., (1986) J. Biol. Chem. 261, 16249–16255) was tested using an identical blot of the avian cDNA-encoded proteins, it detected the recombinant synthase with much higher sensitivity than the avian mitochondrial protein (FIG. 5b). In retrospect, this discrimination, which was consistent with the assignment of the recombinant enzyme as the cytosolic isozyme is quite reasonable. The homology between cytosolic synthases from different eukaryotes (rat vs. chicken, 84% identity) is considerably higher than the homology between cytosolic and mitochondrial proteins from the same species (65% identity for the rat enzymes; Ayte et al., (1990) Proc. Natl. Acad. Sci. USA 87, 3874–3878; Casals et al., 1992, supra). The recombinant enzyme displays a 1.4 fold stimulation of catalytic activity in the presence of Mg$^{2+}$ (Table 2). This behavior, previously reported for the avian cytosolic enzyme (Clinkenbeard et al., 1975, supra), distinguishes it from the mitochondrial isozyme, which is inhibited by Mg$^{2+}$ (Reed et al., 1975, supra). Finally, the empirically determined pI of recombinant synthase (5.8; minor bands at 5.6, 5.4) agreed well with our calculated estimate of pI=5.6 (Kattar-Cooley et al., 1990, supra) as well as empirical estimates for avian (5.2; 5.4; 6.6) and rat (5.4) cytosolic synthases (Clinkenbeard et al., 1975, supra), further distinguishing this protein from the more basic (pI=7.2; Reed et al., 1975, supra) mitochondrial isozyme. Minor proteolysis may account for microheterogeneity apparent in pI determinations.

4. Discussion

In developing a strategy for expression of a recombinant form of avian HMG-CoA synthase, advantage was taken of the fact that the ATG start codon represents half of the Nco I recognition sequence. Modification of the original cDNA to encode a complete Nco I site resulted in a second codon that translates into alanine instead of proline at residue 2. The mature form of the avian mitochondrial enzyme does not contain a corresponding sequence (Kattar-Cooley et al., 1990, supra), yet it functions with catalytic efficiency that is comparable to the cytosolic enzyme. In a sequence deduced from cDNA proposed to encode the precursor form of rat mitochondrial synthase (Ayte et al. 1990, supra), the N-terminus of the mature protein was not directly identified but a conserved proline did not appear in the vicinity of the region generally expected to represent the N-terminus of the processed matrix protein. The validation of this strategy for expression of functional synthase is apparent upon comparison of the properties of isolated avian liver and recombinant enzymes, which is facilitated by the high level of expression and stability of the latter protein. Regardless of whether catalytic efficiency, substrate binding, or Mg$^{2+}$ stimulation are considered, recombinant enzyme faithfully reflects the homologously expressed avian protein.

The partial reactions catalyzed by HMG-CoA synthase are valuable tools for characterizing the recombinant enzyme, regardless of whether it represents wild type protein or an engineered variant. In the absence of co-substrate, HMG-CoA synthase hydrolyzes acetyl-CoA (Miziorko et al., 1975, supra). In catalyzing this partial reaction, it is similar to chloramphenicol acetyltransferase, although that protein's relative rate of hydrolysis (0.1% of overall reaction; Kleanthous, et al., (1984) Biochem. J. 223, 211–220) is lower than the 1% relative hydrolysis rate reported for HMG-CoA synthase (Miziorko et al., 1975, supra). Such hydrolysis is not unexpected, given the thioesterase activity inherent in synthase (cf. eqn.3). The excellent agreement not only between relative rates of hydrolysis catalyzed by avian and recombinant synthases (Table 2) but also between their respective $K_{mAc-CoA}$'s in this partial reaction certainly supports the use of recombinant protein as an experimental model. Additional support derives from the enzymes' acetylation partial reaction (eqn. 1); covalently bound acetyl groups can be trapped with good stoichiometry on both homologously and heterologously expressed synthases.

I claim:

1. A preparation of recombinant avian cytosolic 3-hydroxy-3-methylglutaryl-CoA synthase, wherein the synthase is recombinantly produced in a transformed *E. Coli* BL21(DE3) host cell by the inducible transcriptional activity of a bacteriophage T7 RNA polymerase, wherein the preparation has at least 0.24 units/mg specific activity, wherein at least 90% of the synthase molecules have not been substantially proteolytically cleaved, and wherein the preparation retains 50% activity after storage at 4° C. for six months.

2. The preparation of claim 1 wherein the preparation retains 50% activity after 1 year of storage at 4° C.

3. A preparation of recombinant avian cytosolic HMG-CoA synthase according to claim 1, wherein a crude cell extract is initially formed and wherein the crude extract has at least 0.24 units/mg specific activity.

4. The crude preparation of claim 3 wherein at least 90% of the synthase molecules have not been substantially proteolytically cleaved.

5. A method of evaluating a candidate drug for inhibiting cellular cholesterol synthesis comprising the steps of exposing the candidate drug to the preparation of claim 1 and an HMG-CoA synthase substrate and measuring the decrease in HMG-CoA synthase activity.

* * * * *